United States Patent
Tsubokura et al.

(10) Patent No.: US 10,717,705 B2
(45) Date of Patent: Jul. 21, 2020

(54) METHOD FOR PRODUCING FLUORINE-CONTAINING SULFONYLAMIDE COMPOUND

(71) Applicant: NIPPON SODA CO., LTD., Tokyo (JP)

(72) Inventors: Shiro Tsubokura, Takaoka (JP); Yuka Aomori, Takaoka (JP); Satoshi Kako, Takaoka (JP)

(73) Assignee: NIPPON SODA CO., LTD., Tokyo (JP)

( * ) Notice: Subject to any disclaimer, the term of this patent is extended or adjusted under 35 U.S.C. 154(b) by 0 days.

(21) Appl. No.: 16/318,211

(22) PCT Filed: Aug. 1, 2017

(86) PCT No.: PCT/JP2017/027900
§ 371 (c)(1),
(2) Date: Jan. 16, 2019

(87) PCT Pub. No.: WO2018/034145
PCT Pub. Date: Feb. 22, 2018

(65) Prior Publication Data
US 2019/0233368 A1 Aug. 1, 2019

(30) Foreign Application Priority Data
Aug. 19, 2016 (JP) ................................. 2016-161295

(51) Int. Cl.
*C07C 303/44* (2006.01)
*C01B 21/093* (2006.01)
*C01B 21/086* (2006.01)

(52) U.S. Cl.
CPC .......... *C07C 303/44* (2013.01); *C01B 21/086* (2013.01); *C01B 21/093* (2013.01)

(58) Field of Classification Search
None
See application file for complete search history.

(56) References Cited

U.S. PATENT DOCUMENTS

| 5,916,475 A | 6/1999 | Michot et al. |
| 6,596,772 B1 * | 7/2003 | Huang ................... C07C 311/09 514/602 |
| 9,242,862 B2 | 1/2016 | Tsubokura et al. |
| 10,128,525 B2 | 11/2018 | Schmidt et al. |
| 2006/0223995 A1 * | 10/2006 | Uchimura ............ C07D 233/54 544/59 |
| 2012/0041233 A1 * | 2/2012 | Sato .................... C01B 21/0935 564/154 |
| 2013/0323154 A1 * | 12/2013 | Tsubokura ............ C07C 303/40 423/386 |

FOREIGN PATENT DOCUMENTS

| CA | 2945872 A1 | 10/2015 |
| CN | 103347811 A | 10/2013 |
| EP | 2 505 551 A1 | 10/2012 |
| EP | 2 674 395 A1 | 12/2013 |
| JP | H8-511274 A | 11/1996 |
| JP | 2006-210331 A | 8/2006 |
| JP | 2008-291231 | 12/2008 |
| JP | 2012-136429 A | 7/2012 |
| WO | 2012/108284 A1 | 8/2012 |
| WO | 2012/160280 A2 | 11/2012 |
| WO | 2015/158979 A1 | 10/2015 |
| WO | 2016/093399 A1 | 6/2016 |

OTHER PUBLICATIONS

The 68th Meeting of the Electrochemical Society of Japan, Effect of Imide Salt Purity in Eletroclytes on Charge-Discharge Performance of Negative Electrodes for Lithium Secondary Batteries., Summary of Lectures, p. 232, 2001.
Oct. 17, 2017 International Search Report isssued in International Patent Application No. PCT/JP2017/027900.

* cited by examiner

*Primary Examiner* — Amy C Bonaparte
(74) *Attorney, Agent, or Firm* — Oliff PLC

(57) ABSTRACT

A method for efficiently removing impurities such as sodium ions, fluoride ions, chloride ions and fluorosulfate ions without reducing the yield of a target product, including a fluorine-containing sulfonylamide compound selected from the group consisting of fluorine-containing sulfonylamide, a metal salt thereof, an ammonium salt thereof and a quaternary ammonium salt thereof is washed with an aqueous solution of salt of sulfuric acid.

2 Claims, No Drawings

METHOD FOR PRODUCING FLUORINE-CONTAINING SULFONYLAMIDE COMPOUND

TECHNICAL FIELD

The present invention relates to a method for producing a fluorine-containing sulfonylamide compound.

This application claims priority to Japanese Patent Application No. 2016-161295 filed on Aug. 19, 2016, the disclosure of which is hereby incorporated by reference.

BACKGROUND ART

Fluorine-containing sulfonylamide salts are a compound useful as an ion conductive material, and an electrolyte or an additive used in secondary batteries or the like (Patent Document 1, Patent Document 2).

It has been reported that the more impurities such as water, ash and $SO_4^{2-}$ contained in those salts are reduced, the higher the effect on discharge capacity and current efficiency in charge-discharge of secondary batteries becomes (Non-patent Document 1). Thus, methods for producing such salts in high purity have been developed.

For example, a method for producing high purity fluorosulfonylamide salt in which after fluorination reaction of chlorosulfonylamide or a salt thereof, the reaction solution is contacted with an alkaline aqueous solution to remove impurities has been proposed (Patent Document 3).

PRIOR ART DOCUMENTS

Patent Documents

Patent Document 1: Japanese unexamined Patent Application Publication (Translation of PCT Application) No. 08-511274
Patent Document 2: Japanese unexamined Patent Application Publication No. 2006-210331
Patent Document 3: Japanese unexamined Patent Application Publication No. 2012-136429

Non-Patent Documents

Non-patent Document 1: The 68th Meeting of the Electrochemical Society of Japan, Meeting Abstract, p. 232 (2001)

SUMMARY OF THE INVENTION

Object to be Solved by the Invention

There has been a problem even in the above method for producing high purity fluorosulfonylamide salt in that, for example, fluoride ions remaining after the reaction of replacing chlorine atoms with fluorine atoms corrode the glass lining tank (GL tank) which is the reactor in the subsequent step and impurities such as sodium ions are increased.

Furthermore, in some cases, a small amount of fluorosulfuric acid comes in contact with an alkaline aqueous solution and thus salt of fluorosulfuric acid is formed and mixed in the target product. Such impurities can be removed by washing with water, but the problem is that since the target product is water-soluble, the yield is reduced. In addition, salt of fluorosulfuric acid therein is decomposed into fluoride ions which become impurities, and as described above, there was also a possibility that impurities such as sodium ions are increased by corroding the GL tank which is the reactor with the resulting fluoride ions. Mixing of such impurities may result in a reduced quality of fluorine-containing sulfonylamide compounds.

An object of the present invention is to provide a method for efficiently removing impurities such as sodium ions, fluoride ions, chloride ions and fluorosulfate ions without reducing the yield of a target product.

Means to Solve the Object

The present inventors have conducted intensive studies to solve the above object, and as a result have been found that the object is achieved by washing a fluorine-containing sulfonylamide compound with a specific aqueous salt solution, and the present invention has been completed.

Accordingly, the present invention includes the following.

(1) A method for producing a fluorine-containing sulfonylamide compound, comprising a step of washing a fluorine-containing sulfonylamide compound selected from the group consisting of fluorine-containing sulfonylamide, a metal salt thereof, an ammonium salt thereof and a quaternary ammonium salt thereof with the use of an aqueous solution of salt of sulfuric acid.

(2) The method for producing a fluorine-containing sulfonylamide compound according to (1), wherein the step of washing a fluorine-containing sulfonylamide compound with an aqueous solution of salt of sulfuric acid is performed after a chlorine atom of a chlorine-containing sulfonylamide compound selected from the group consisting of chlorine-containing sulfonylamide, a metal salt thereof, an ammonium salt thereof and a quaternary ammonium salt thereof is replaced with a fluorine atom using a fluorinating agent.

(3) The method for producing a fluorine-containing sulfonylamide compound according to (1) or (2), comprising a step of neutralization before the step of washing with an aqueous solution of salt of sulfuric acid.

(4) The method for producing a fluorine-containing sulfonylamide compound according to (2), wherein the fluorinating agent is at least one selected from the group consisting of hydrogen fluoride, metal fluoride, ammonium fluoride, ammonium fluoride-mono or -poly(hydrogen fluoride) complex, quaternary ammonium fluoride and quaternary ammonium fluoride-mono or -poly(hydrogen fluoride) complex.

(5) The method for producing a fluorine-containing sulfonylamide compound according to any one of (1) to (4), wherein the fluorine-containing sulfonylamide compound is a compound represented by Formula [II]:

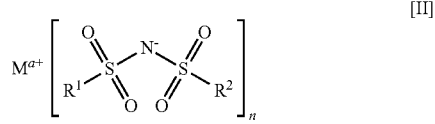

(wherein $R^1$ represents a fluorinated alkyl group having 1 to 6 carbon atoms or a fluorine atom; $R^2$ represents a chlorine atom or a fluorine atom; M represents a hydrogen atom, a metal atom, an ammonium cation residue or a quaternary ammonium cation residue; and when M is a hydrogen atom, n is 1; when M is a metal atom, represents a valence of the metal atom; and when M is an ammonium cation residue or a quaternary ammonium residue, n is 1).

(6) The method for producing a fluorine-containing sulfonylamide compound according to any one of (1) to (5), wherein the fluorine-containing sulfonylamide is bis(fluorosulfonyl)amide.

Effect of the Invention

According to the present invention, a fluorine-containing sulfonylamide compound may be produced in good yield and high purity because impurities such as metal ions and fluoride ions, which degrade properties of electrolyte, may be industrially efficiently reduced by washing a fluorine-containing sulfonylamide compound with an aqueous solution of salt of sulfuric acid.

Mode of Carrying Out the Invention

The fluorine-containing sulfonylamide compound according to the present invention means a compound selected from the group consisting of fluorine-containing sulfonylamide, a metal salt thereof, an ammonium salt thereof and a quaternary ammonium salt thereof.

The structure of fluorine-containing sulfonylamide is not particularly limited as long as fluorine-containing sulfonylamide contains a fluorine atom and a sulfonylamide bond in the molecule. Specific examples thereof may include compounds represented by the following Formula [I]:

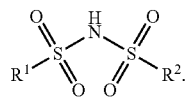

In the formula, $R^1$ represents a fluorinated alkyl group having 1 to 6 carbon atoms or a fluorine atom and $R^2$ represents a chlorine atom or a fluorine atom. In $R^1$, as the fluorinated alkyl group having 1 to 6 carbon atoms, fluoromethyl group, difluoromethyl group, trifluoromethyl group, fluoroethyl group, difluoroethyl group, 2,2,2-trifluoroethyl group, pentafluoroethyl group, 3,3,3-trifluoropropyl group, perfluoro-n-propyl group, fluoropropyl group, perfluoroisopropyl group, fluorobutyl group, 3,3,4,4,4-pentafluorobutyl group, perfluoro-n-butyl group, perfluoroisobutyl group, perfluoro-t-butyl group, perfluoro-sec-butyl group, fluoropentyl group, perfluoropentyl group, perfluoroisopentyl group, perfluoro-t-pentyl group, fluorohexyl group, perfluoro-n-hexyl group, perfluoroisohexyl group or the like may be specifically exemplified. As Formula [I], bis(fluorosulfonyl)amide, bis(trifluoromethylsulfonyl)amide, N-trifluoromethylsulfonyl-N-fluorosulfonylamide or the like may be specifically exemplified.

As the fluorine-containing sulfonyl compound other than fluorine-containing sulfonylamide, compounds represented by Formula [II] may be specifically exemplified.

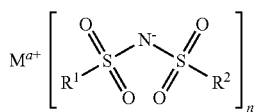

In Formula [II], $R^1$ and $R^2$ are as defined in Formula [I]. M represents a hydrogen atom, a metal atom, an ammonium cation residue or a quaternary ammonium cation residue; and when M is a hydrogen atom, n is 1, when M is a metal atom, n represents a valence of the metal atom, and when M is an ammonium cation residue or a quaternary ammonium residue, n is 1. As the metal atom M in Formula [II], potassium, sodium, lithium, zinc or the like may be specifically exemplified. As the quaternary ammonium residue, tetramethylammonium, tetrabutylammonium or the like may be exemplified. The residue means a moiety constituting a cation other than charge. As the compound represented by Formula [II], bis(fluorosulfonyl)amide potassium salt, N-(fluorosulfonyl)-N-(trifluoromethylsulfonyl)amide potassium salt, bis(fluorosulfonyl)amide sodium salt, N-(fluorosulfonyl)-N-(trifluoromethylsulfonyl)amide sodium salt, bis(fluorosulfonyl)amide lithium salt, N-(fluorosulfonyl)-N-(trifluoromethylsulfonyl)amide lithium salt, bis(bis(fluorosulfonyl)amide)zinc salt, bis(N-(fluorosulfonyl)-N-(trifluoromethylsulfonyl)amide)zinc salt, bis(fluorosulfonyl)amide ammonium salt, N-(fluorosulfonyl)-N-(trifluoromethylsulfonyl)amide ammonium salt, N-(fluorosulfonyl)-N-(pentafluoroethylsulfonyl)amide ammonium salt, N-(fluorosulfonyl)-N-(perfluoro-n-propylsulfonyl)amide ammonium salt, bis(fluorosulfonyl)amide tetramethylammonium salt, N-(fluorosulfonyl)-N-(trifluoromethylsulfonyl)amide tetramethylammonium salt, bis(fluorosulfonyl)amide tetrabutylammonium salt, N-(fluorosulfonyl)-N-(trifluoromethylsulfonyl)amide tetrabutylammonium salt or the like may be specifically exemplified.

Of them, bis(fluorosulfonyl)amide ammonium salt is preferred.

The fluorine-containing sulfonylamide compound may be prepared by a known method. In particular, a method in which chlorine-containing sulfonylamide in which a chlorine atom is at the position of fluorine atom is subjected to fluorine replacement using fluorinating agent may be preferably exemplified. As a specific method thereof, a method in which chlorine atoms of bis(chlorosulfonyl)amide prepared by a known method are substituted with fluorine atoms using a fluorinating agent, a method in which neutralization is performed after fluorine replacement or a method in which bis(chlorosulfonyl)amide is neutralized to form a salt and then chlorine atoms are substituted with fluorine atoms using a fluorinating agent may be exemplified.

As the fluorinating agent used in fluorine substitution, hydrogen fluoride, metal fluoride, ammonium fluoride, ammonium fluoride-mono or -poly(hydrogen fluoride) complex, quaternary ammonium fluoride, quaternary ammonium fluoride-mono or -poly(hydrogen fluoride) complex or the like may be specifically exemplified. In particular, ammonium fluoride, and ammonium fluoride-mono or -poly(hydrogen fluoride) complex are preferred.

The reaction between fluorine-containing sulfonylamide represented by Compound (I) or a fluorine-containing sulfonyl compound represented by Compound (II) and a fluorinating agent is carried out by mixing Compound (I) or (II) with the fluorinating agent in a solvent.

In the reaction, the fluorinating agent may be dissolved or suspended in a solvent to be used or may be melted by heating to be used.

The solvent for dissolving or suspending the fluorinating agent is not particularly limited as long as the solvent does not inhibit the fluorination reaction.

As the solvent, an aprotic solvent such as ethylene carbonate, propylene carbonate, butylene carbonate, γ-butyrolactone, γ-valerolactone, dimethoxymethane, 1,2-dimethoxyethane, tetrahydrofuran, 2-methyl tetrahydrofuran, 1,3-dioxane, 4-methyl-1,3-dioxolane, methyl formate, methyl acetate, methyl propionate, dimethyl carbonate, ethyl methyl carbonate, diethyl carbonate, sulfolane, 3-methyl sulfolane, dimethyl sulfoxide, N,N-dimethylformamide, N-methyl oxazolidinone, acetonitrile, valeronitrile, benzonitrile, ethyl acetate, isopropyl acetate, butyl acetate, nitromethane, nitrobenzene, toluene, methylene chloride, carbon tetrachloride, chloroform or the like may be exemplified. Polar solvents are preferably used for a smooth progress of fluorination reaction. As a preferred solvent, acetonitrile, ethyl acetate, isopropyl acetate or butyl acetate may be exemplified.

In the step of washing a fluorine-containing sulfonylamide compound with an aqueous solution of salt of sulfuric acid, methods thereof are not particularly limited and may include a method in which a fluorine-containing sulfonylamide compound is dissolved in the above solvent and washing is performed by adding an aqueous solution of salt of sulfuric acid thereto, or by adding the resulting solution to the aqueous solution of salt of sulfuric acid, and then mixing. It is particularly preferable that in the step, a reaction solution of a fluorine-containing sulfonyl compound which has been produced by the above method of substituting chlorine atoms with fluorine atoms is washed with an aqueous solution of salt of sulfuric acid. Furthermore, it is preferable that in the case of performing cation exchange reaction using a fluorine-containing compound, the washing step is provided before the cation exchange reaction.

The amount used of salt of sulfuric acid is not particularly limited, but is in the range of preferably 0.01 to 10 moles, more preferably 0.05 to 5 moles, and further preferably 0.1 to 2 moles with respect to 1 mole of the fluorine-containing sulfonylamide compound.

The concentration of the aqueous solution of salt of sulfuric acid is not particularly limited, but is preferably in the range of 5 to 30% by mass, and further preferably in the range of 10 to 20% by mass. When the concentration is less than 5% by mass, the target product tends to be dissolved in the aqueous phase, causing the yield to be reduced. When the concentration is more than 30% by mass, complete elimination of impurities tends to be difficult.

The washing step may be performed once or divided into a few steps.

Inorganic sulfate is used as the salt of sulfuric acid for washing, and examples thereof include metal sulfates such as sodium sulfate, potassium sulfate, lithium sulfate, barium sulfate, magnesium sulfate and calcium sulfate; ammonium sulfate; hydrogen sulfates such as sodium hydrogen sulfate and potassium hydrogen sulfate; and double salts such as alum.

It is preferable that salt of sulfuric acid is selected according to the object to be washed. Those with the same counter cation as that in a fluorine-containing sulfonylamide compound, which is the object to be washed, are preferred. For example, it is preferable that an aqueous ammonium sulfate solution is used for fluorine-containing sulfonylamide ammonium salt and an aqueous metal sulfate solution is used for fluorine-containing sulfonylamide metal salt.

As impurities in the fluorine-containing sulfonylamide compound, which are to be removed, ions of atoms such as sodium, potassium, boron, magnesium, calcium, silicon, titanium, zirconium, vanadium, chromium, molybdenum, tungsten, manganese, iron, cobalt, nickel, copper, zinc, aluminum, lead, bismuth, fluorine, chlorine, bromine and iodine, ions of atomic groups containing the above, and ions such as fluorosulfric ion and ammonium ion may be exemplified.

It is preferable that as few ions to be removed as possible are incorporated into an aqueous solution of salt of sulfuric acid. For example, when sodium ions are to be removed, an aqueous solution of salt of sulfuric acid in which the concentration of sodium ion is 5 ppm or less is preferably used.

The temperature for washing is 0 to 60° C., preferably 0 to 40° C., and further preferably 10 to 30° C.

The present invention is capable of reducing fluoride ions significantly, and thus when steps following fluorination are performed in a reaction vessel composed of glass layer which is greatly damaged by fluoride ions, e.g., a GL tank, not only damage in the GL tank can be prevented but also incorporation of impurities such as sodium ions dissolved due to remaining fluorine ions into products can be prevented, and thus the present invention is particularly useful.

The method for the production of the present invention is very useful for efficiently removing impurities such as sodium ions mixed in a fluorine-containing sulfonylamide compound. Since the amount mixed of metal impurities which degrade properties of electrolyte is smaller in the fluorine-containing sulfonylamide compound obtained by the method for the production of the present invention than that in a compound prepared by a conventional method, the fluorine-containing sulfonylamide compound may be suitably used as an ion conductive material or an intermediate thereof constituting an electrochemical device such as a primary battery, a secondary battery such as a lithium ion secondary battery, an electrolytic condenser, an electric double layer capacitor, a fuel cell, a solar battery and an electrochromic element.

EXAMPLES

Hereinafter, the present invention will be explained more specifically below referring to the following Examples. The present invention is not intended to be limited to the following examples, and can, of course, be practiced with modification as appropriate within a range that can be adaptable to the purposes of the present invention, and those are all encompassed in the technical scope of the present invention.

Example 1

The amount of sodium ions in bis(fluorosulfonyl)amide ammonium salt was previously determined by cation chromatography to be 35 ppm. 303.61 g of a butyl acetate solution containing 39.71 g of the bis(fluorosulfonyl)amide ammonium salt was washed with 66.25 g of a 20% by mass aqueous ammonium sulfate solution containing 0.5 molar equivalent of ammonium sulfate with respect to the bis(fluorosulfonyl)amide ammonium salt, and separated to give 305.80 g of a butyl acetate solution containing 37.89 g (yield 95.4%) of bis(fluorosulfonyl)amide ammonium salt. 10.58 g of the solution was sampled, and the solvent was removed in vacuo, and the amount of sodium ions was determined by cation chromatography to be 13 ppm.

The amount of impurities, sodium ions, was significantly reduced by washing bis(fluorosulfonyl)amide ammonium salt with an aqueous ammonium sulfate solution while suppressing degradation of the target product.

Example 2

295.22 g of a butyl acetate solution containing 36.58 g of the bis(fluorosulfonyl)amide ammonium salt prepared in Example 1 was washed with 64.81 g of a 20% by mass aqueous ammonium sulfate solution containing 0.5 molar equivalent of ammonium sulfate with respect to the bis (fluorosulfonyl)amide ammonium salt, and separated to give 291.21 g of a butyl acetate solution containing 33.29 g (yield 91.0%) of bis(fluorosulfonyl)amide ammonium salt. 10.13 g of the solution was sampled, and the solvent was removed in vacuo, and the amount of sodium ions was determined by cation chromatography to be 4 ppm.

Comparative Example 1

Experiment was performed in the same manner as in Example 1 except for using, instead of the aqueous ammonium sulfate solution, 26.73 g of a 20% by mass aqueous ammonium chloride solution containing 1.0 molar equivalent of ammonium chloride with respect to the bis(fluorosulfonyl)amide ammonium salt for 152.23 g of a butyl acetate solution containing 19.82 g of the bis(fluorosulfonyl) amide ammonium salt. As a result, 151.90 g of a butyl acetate solution containing 18.87 g (yield 95.2%) of bis (fluorosulfonyl)amide ammonium salt was obtained. The amount of sodium ions in the solution was determined by cation chromatography to be 22 ppm.

Comparative Example 2

Experiment was performed in the same manner as in Example 2 except for using, instead of the aqueous ammonium sulfate solution, 24.89 g of a 20% by mass aqueous ammonium chloride solution containing 1.0 molar equivalent of ammonium chloride with respect to the bis(fluorosulfonyl)amide ammonium salt for 141.09 g of a butyl acetate solution containing 17.52 g of the bis(fluorosulfonyl) amide ammonium salt prepared in Comparative Example 1. As a result, 139.16 g of a butyl acetate solution containing 16.13 g (yield 92.1%) of bis(fluorosulfonyl)amide ammonium salt was obtained. The amount of sodium ions in the solution was determined by cation chromatography to be 15 ppm.

Example 3

The amount of sodium ions in bis(fluorosulfonyl)amide lithium salt was previously determined by cation chromatography to be 23 ppm. 137.86 g of a butyl acetate solution containing 17.18 g of the bis(fluorosulfonyl)amide lithium salt was washed with 25.67 g of a 20% by mass aqueous lithium sulfate solution containing 0.5 molar equivalent of lithium sulfate with respect to the bis(fluorosulfonyl)amide lithium salt, and separated to give 146.11 g of a butyl acetate solution containing 16.92 g (yield 98.5%) of bis(fluorosulfonyl)amide lithium salt. 12.69 g of the solution was sampled, and the solvent was removed in vacuo, and the amount of sodium ions was determined by cation chromatography to be 15 ppm. The amount of impurities, sodium ions, was significantly reduced by washing bis(fluorosulfonyl)amide lithium salt with an aqueous lithium sulfate solution while suppressing degradation of the target product.

Example 4

The amount of sodium ions in bis(fluorosulfonyl)amide ammonium salt was previously determined by cation chromatography to be 5 ppm, and the amount of fluoride ions, chloride ions and fluorosulfric ions ($FSO_3^-$) was previously determined by anion chromatography to be 1179 ppm, 24 ppm, 1378 ppm, respectively.

56.37 g of butyl acetate was added to 95.64 g of a butyl acetate solution containing 19.81 g of the bis(fluorosulfonyl) amide ammonium salt (sample A). Then the mixture was washed with 33.08 g of a 20% by mass aqueous ammonium sulfate solution containing 0.5 molar equivalent of ammonium sulfate with respect to the bis(fluorosulfonyl)amide ammonium salt, and separated to give 152.24 g of a butyl acetate solution containing 17.84 g (yield 90.1%) of bis (fluorosulfonyl)amide ammonium salt. After that, 142.69 g of the butyl acetate solution containing 16.72 g of the bis(fluorosulfonyl)amide ammonium salt was washed with 31.00 g of a 20% by mass aqueous ammonium sulfate solution containing 0.5 molar equivalent of ammonium sulfate with respect to the bis(fluorosulfonyl)amide ammonium salt, and separated to give 140.14 g of a butyl acetate solution containing 14.92 g (yield 89.2%) of bis(fluorosulfonyl)amide ammonium salt (sample B).

Part of the solution was sampled, and the solvent was removed in vacuo, and the amount of sodium ions (determined by cation chromatography), fluoride ions, chloride ions and fluorosulfate ions ($FSO_3^-$) (determined by anion chromatography) was 1 ppm, 5 ppm, 3 ppm, 22 ppm, respectively.

The amount of impurities such as fluoride ions, in addition to sodium ions, was significantly reduced by washing bis (fluorosulfonyl)amide ammonium salt with an aqueous ammonium sulfate solution.

Example 5

A GL test piece experiment was performed using sample B which was obtained by washing of sample A and used in Example 4.

A GL test piece was placed in a plastic container and 42.58 g of sample B was added to the container so that the liquid contact area of the GL test piece was 14 cm². The test piece was left to stand at 25° C.

Part of the solution was sampled 0 day and 1 day after being left to stand, and the solvent was removed in vacuo, and the amount of sodium ions was measured by cation chromatography. The result was <1 ppm, <1 ppm, respectively, in sample B. No increase was observed.

The amount of impurities such as fluoride ions was significantly reduced by washing with an aqueous ammonium sulfate solution, and thus corrosion of GL and the resulting increase of sodium ions were suppressed.

Comparative Example 3

A GL test piece experiment was performed in the same manner as in Example 5 except for using 46.14 g of a solution whose composition was the same as that of sample A instead of sample B.

Part of the solution was sampled 0 day and 1 day after being left to stand, and the solvent was removed in vacuo, and the amount of sodium ions was measured by cation exchange chromatography. The result was 5 ppm, 30 ppm, respectively, in sample A. A significant increase was observed.

The invention claimed is:
1. A method for producing a fluorine-containing sulfonylamide compound, the method comprising:
    mixing a fluorine-containing sulfonylamide compound represented by Formula [II]:

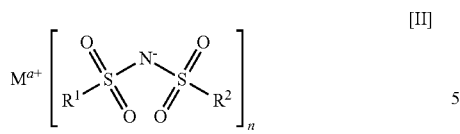

wherein
- $R^1$ represents a fluorinated alkyl group having 1 to 6 carbon atoms or a fluorine atom;
- $R^2$ represents a chlorine atom or a fluorine atom;
- M represents a lithium atom or an ammonium cation residue, and
- n is 1, with an aqueous solution of a salt of sulfuric acid selected from the group consisting of lithium sulfate and ammonium sulfate; and then
- removing the aqueous solution of a salt of sulfuric acid from the fluorine-containing sulfonylamide compound represented by Formula [II],
- wherein:
- when M is a lithium atom, the salt of sulfuric acid is lithium sulfate, and
- when M is an ammonium cation residue, the salt of sulfuric acid is ammonium sulfate.

2. The method for producing a fluorine-containing sulfonylamide compound according to claim 1, wherein the fluorine-containing sulfonylamide compound is a lithium or ammonium salt of bis(fluorosulfonyl)amide.

* * * * *